US010434001B2

United States Patent
Wang

(10) Patent No.: US 10,434,001 B2
(45) Date of Patent: Oct. 8, 2019

(54) ANKLE BRACE

(71) Applicant: Yu-Chien Wang, Taichung (TW)

(72) Inventor: Yu-Chien Wang, Taichung (TW)

( * ) Notice: Subject to any disclaimer, the term of this patent is extended or adjusted under 35 U.S.C. 154(b) by 401 days.

(21) Appl. No.: 15/429,648

(22) Filed: Feb. 10, 2017

(65) Prior Publication Data

US 2018/0228634 A1 Aug. 16, 2018

(51) Int. Cl.
*A61F 5/00* (2006.01)
*A61F 5/01* (2006.01)

(52) U.S. Cl.
CPC ..... *A61F 5/0111* (2013.01); *A61F 2005/0174* (2013.01); *A61F 2005/0181* (2013.01)

(58) Field of Classification Search
CPC ........ A61F 5/01; A61F 5/0102; A61F 5/0111; A61F 5/0113; A61F 5/0127
USPC .......................... 602/27, 28–29, 13; D24/192
See application file for complete search history.

(56) References Cited

U.S. PATENT DOCUMENTS

| | | | | |
|---|---|---|---|---|
| 4,964,402 A * | 10/1990 | Grim | ..................... | A61F 5/0111 602/2 |
| 4,966,134 A * | 10/1990 | Brewer | ................. | A61F 5/0111 128/882 |
| 5,501,659 A * | 3/1996 | Morris | ................... | A61F 5/0111 128/882 |
| 5,709,650 A * | 1/1998 | Colman | ................ | A61F 5/0111 128/DIG. 15 |
| 6,554,785 B1 * | 4/2003 | Sroufe | ................... | A61F 5/0111 128/882 |
| 7,018,351 B1 * | 3/2006 | Iglesias | ................. | A61F 5/0111 128/882 |
| 7,662,117 B2 * | 2/2010 | Parizot | ................... | A61F 5/0111 602/13 |
| 2007/0049855 A1 * | 3/2007 | Mattear | ................. | A61F 5/0111 602/27 |

* cited by examiner

*Primary Examiner* — Kim M Lewis
(74) *Attorney, Agent, or Firm* — Muncy, Geissler, Olds & Lowe, P.C.

(57) ABSTRACT

An ankle brace is provided, including a main body. The main body has a base portion and an abutting portion for abutting against an ankle, the base portion has at least one first guiding slot, the at least one first guiding slot is arranged next to the abutting portion, the abutting portion has a bottom portion, a circumferential side portion which surrounds and is connected to and between the bottom portion and the base portion and at least one second guiding slot, the bottom portion has a receiving space for receiving a part of the ankle, the circumferential side portion projects above a slot bottom of the first guiding slot, and the at least one second guiding slot is arranged on the bottom portion and penetrates the circumferential side portion and communicated with the at least one of the first guiding slots.

10 Claims, 6 Drawing Sheets

ANKLE BRACE

BACKGROUND OF THE INVENTION

Field of the Invention

The present invention relates to a protector, and more particularly to an ankle brace.

Description of the Prior Art

When one is exercising, joints may be injured, especially ankles. To prevent ankles from being injured or to conduct rehabilitation treatment, an ankle brace is developed to be worn on foot to restrict the movement of the ankles and provide a restriction force to resist impacts from outside so that ankles will not be injured due to overexertion and will not be injured again.

However, in this type of ankle brace, the ankle brace is sleeved or wrapped on the ankle with cloth (cloth tangles or cooperates with bandages), and a user is often unable to control a tightness precisely. If it is too loose, the protection effect is insufficient, and if it is too tight, blood circulation of the shank is unsmooth. In addition, the air permeability may be not preferable, and especially when the ankle brace is used with a shell body, skin of the user may feel uncomfortable.

The present invention has arisen to mitigate and/or obviate the afore-described disadvantages.

SUMMARY OF THE INVENTION

The major object of the present invention is to provide an ankle brace, which has an abutting portion abutting against an ankle to provide positioning effect. The ankle brace further has a first and second guiding slots which can adjusted and deformed slightly to be fit to the ankle and ensure air permeability when the ankle brace is worn.

To achieve the above and other objects, an ankle brace is provided, including a main body. The main body has a base portion and an abutting portion for abutting against an ankle, the base portion has at least one first guiding slot, the at least one first guiding slot is arranged next to the abutting portion, the abutting portion has a bottom portion, a circumferential side portion which surrounds and is connected to and between the bottom portion and the base portion and at least one second guiding slot, the bottom portion has a receiving space for receiving a part of the ankle, the circumferential side portion projects above a slot bottom of the first guiding slot, and the at least one second guiding slot is arranged on the bottom portion and penetrates the circumferential side portion and communicated with the at least one of the first guiding slots.

The present invention will become more obvious from the following description when taken in connection with the accompanying drawings, which show, for purpose of illustrations only, the preferred embodiment(s) in accordance with the present invention.

DETAILED DESCRIPTION OF THE PREFERRED EMBODIMENTS

The present invention will be clearer from the following description when viewed together with the accompanying drawings, which show, for purpose of illustrations only, the preferred embodiment in accordance with the present invention.

Figure 1:
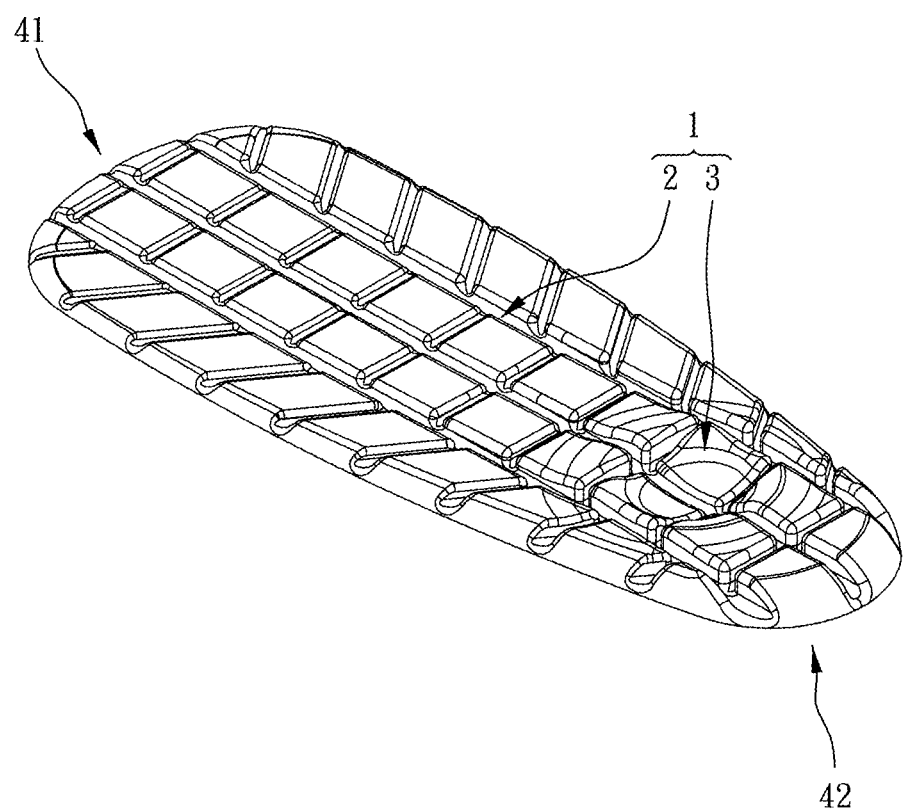
FIG. 1 is a stereogram of an embodiment of the present invention.
Figure 2:
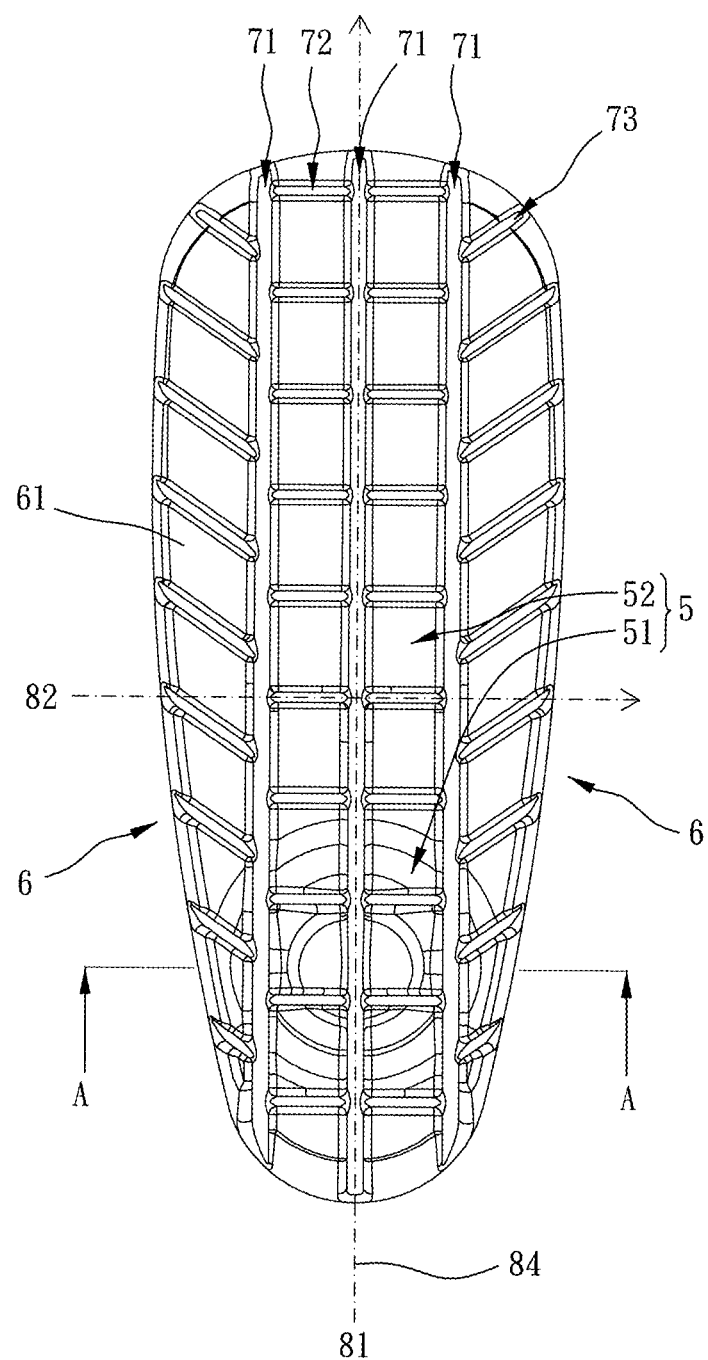
FIG. 2 is a side view of the embodiment of the present invention.
Figure 3:
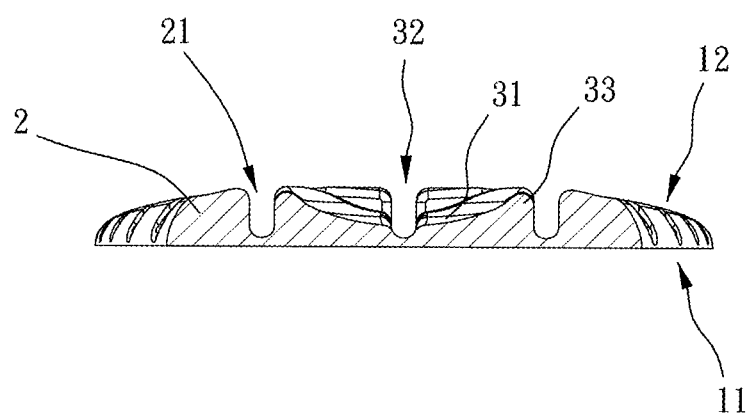
FIGS. 3 and 4 are side views of the embodiment of the present invention.
Figure 4:
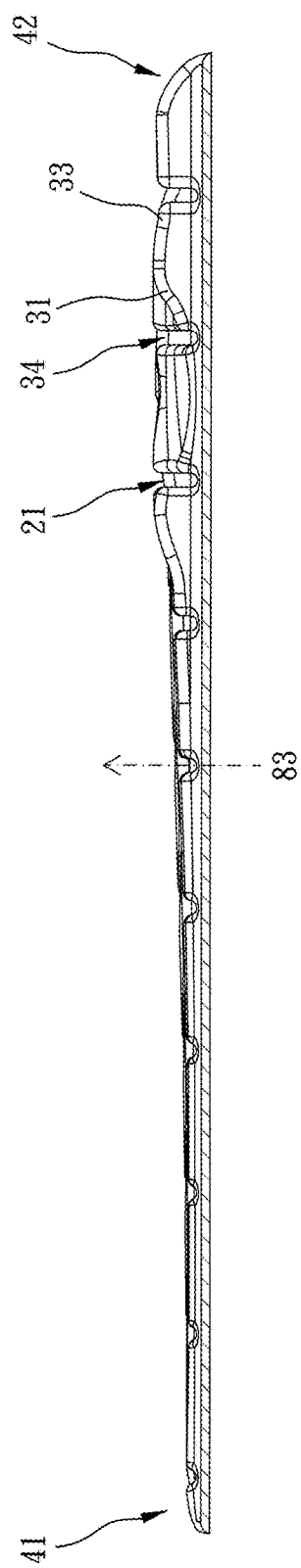
Figure 5:
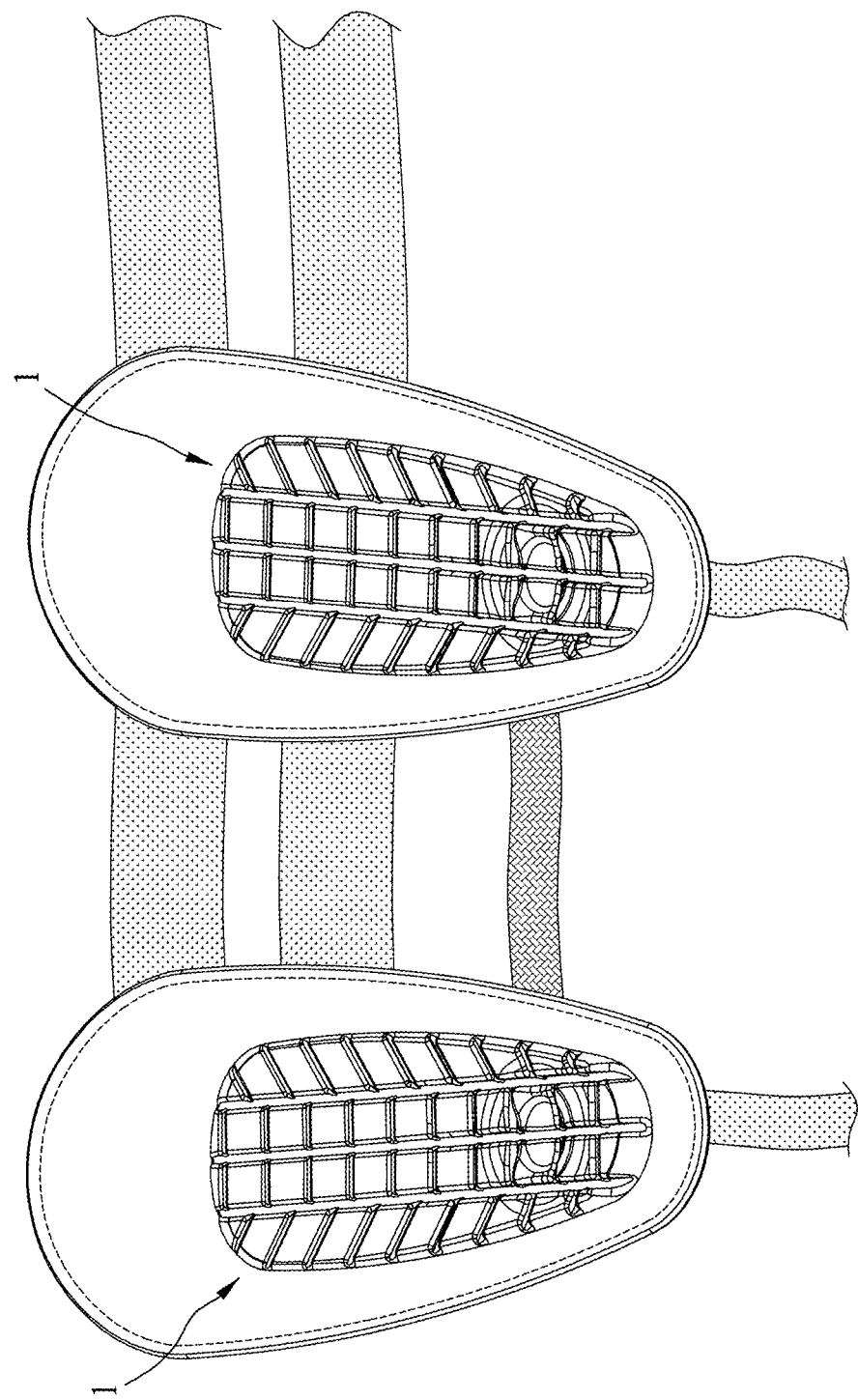
FIG. 5 is an assembly view of the embodiment of the present invention.
Figure 6:
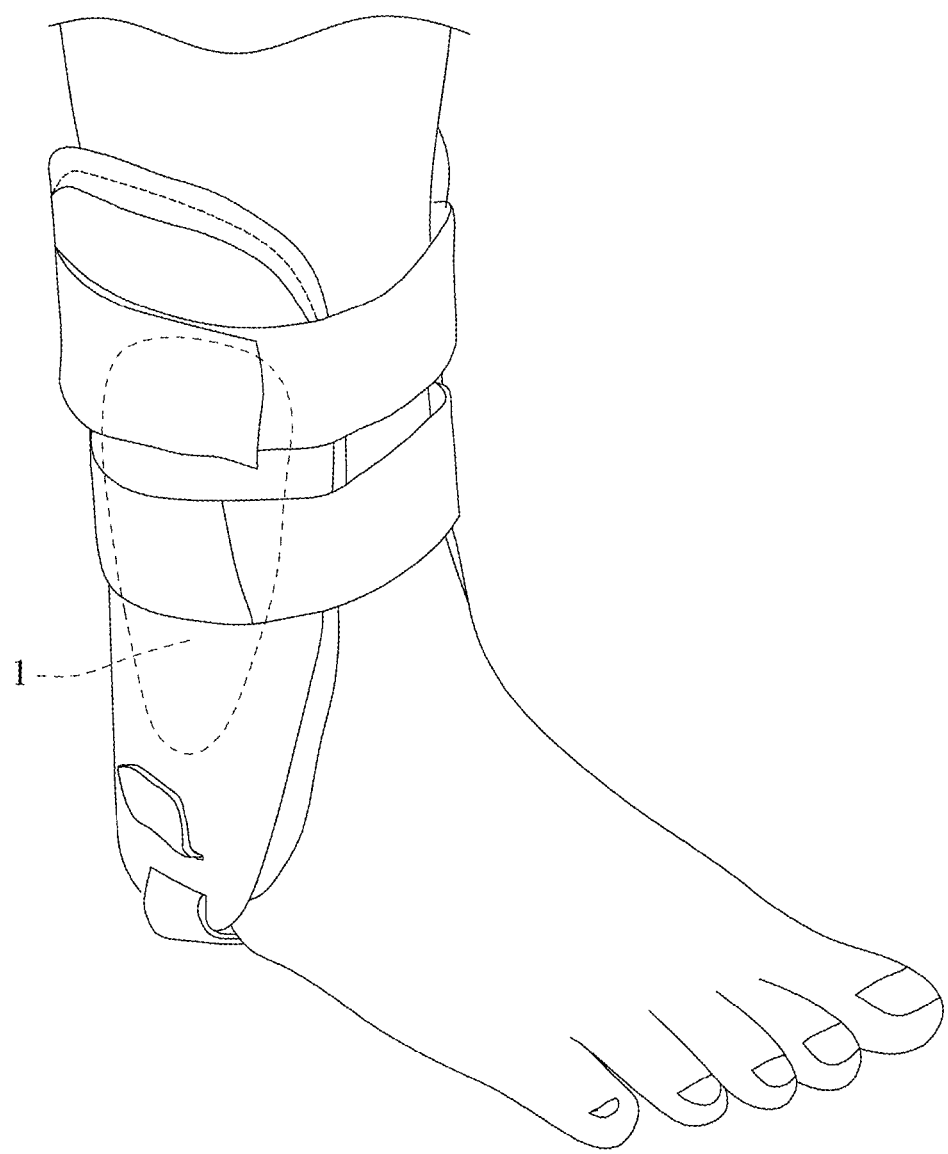
FIG. 6 is a drawing showing the embodiment of the present invention in use.

Please refer to FIGS. 1 to 6 for an embodiment of the present invention. An ankle brace includes a main body 1.

Specifically, the main body 1 has a base portion 2 and an abutting portion 3 for abutting against an ankle, the base portion 2 has at least one first guiding slot 21, the at least one first guiding slot 21 is arranged next to the abutting portion 3, the abutting portion 3 has a bottom portion 31, a circumferential side portion 33 which surrounds and is connected to and between the bottom portion 31 and the base portion 2 and at least one second guiding slot 34, the bottom portion 31 has a receiving space 32 for receiving a part of the ankle, the circumferential side portion 33 projects above a slot bottom of the first guiding slot 21, and the at least one second guiding slot 34 is arranged on the bottom portion 31 and penetrates the circumferential side portion 33 and communicated with the at least one of the first guiding slots 21. The bottom portion 31 is in dented dome shape, and the circumferential side portion 33 and the bottom portion 31 are arranged concentrically.

More specifically, the main body 1 further has a first face 11 and a second face 12 which are opposite to each other, the first face 11 is a plane, the second face 12 is for abutting against a leg, the abutting portion 3 and the at least one first guiding slot 21 are arranged on the second face 12, and an extension direction of the at least one first guiding slot 21 and an extension direction of the at least one second guiding slot 34 are parallel to the first face 11.

Preferably, at least one of the first guiding slots 21 penetrates the base portion 2 to communicate with an outside of the main body so as to directly and quickly exchange fluids. More preferably, the main body 1 is made of at least one of a soft material and a flexible material to provide preferable comfort and fitness and has a buffering effect when being impacted. The material mentioned above may be, for example but not limited thereto, PVC, TPE, NBR, PER, EVA, NR and silicone.

It is to be noted that the main body 1 defines a length direction 81, on the length direction 81, the base portion 2 has a first end portion 41 and a second end portion 42 which are opposite to each other, a distance between the first end portion 41 and the abutting portion 3 is greater than a distance between the second end portion 42 and the abutting portion 3, when in use, the first end portion 41 contacts a shank, and the second end portion contacts the ankle. A thickness of the leg gradually decreases from the shank toward the ankle, and after the ankle is injured, a movement of the ankle needs to be restricted; therefore, preferably, a thickness of the base portion 2 gradually increases from the first end portion 41 toward the abutting portion 3 to protect the ankle. In addition, the main body 1 defines a thickness direction 83, and on the thickness direction 83, the base portion 2 is non-protrusive above the circumferential side portion 33 so as to make sure that after the ankle brace is wore on the leg, a leg circumference is more uniformed, and it is more convenient for the user to bind (with bands or Velcro) the ankle brace. Besides, cooperating of the ankle brace with a shell body (soft/hard) can provide a more preferable engagement.

In this embodiment, a thickness of the second end portion 42 is greater than a thickness of the first end portion 41 and is substantially equal to a thickness of the circumferential side portion 33, and more preferably, the thickness of the second end portion 42 is 2 to 3 times of the thickness of the first end portion 41. In addition, on a width direction 82 of the main body 1, a greatest dimension of the first end portion 41 is 2 to 3 times of a greatest dimension of the second end portion 42.

To analyze an overall structure of the ankle brace, along the length direction 81 of the main body 1, the base portion 2 is divided into a main block 5 and two minor blocks 6, the two minor blocks 6 are symmetrically arranged by two sides of the main block 5, the two minor blocks 6 can be bent to wrap along the leg, and the abutting portion 3 is arranged on the main block 5. In addition, on the width direction 82 of the main body 1, each said minor block 6 is respectively tapered toward the first and second end portions 41, 42. Moreover, a part of the main block 5 which has the abutting portion 3 is defined as a first block 51, and the rest part of the main body 5 is defined as a second block 52; and an inner portion 61 of each said minor block 6 corresponds to the second block 52 on a width direction 82 of the main body 1, and on the width direction 82 of the main body 1, a thickness of each said inner portion 61 gradually decreases toward the second block 52 so that each said minor block 6 can be easily bent relative to the main block 5 to match a shape of the leg.

More specifically, a number of the at least one first guiding slot 21 is plural; the main block 5 has a plurality of first passages 71 and a plurality of second passages 72, the first passages 71 extend along the length direction 81 of the main body 1 and penetrate the base portion 2, the second passages 72 are perpendicular to the first passages 71 and communicate with the first passages 71, each said minor block 6 has a plurality of third passages 73, the third passages 73 are slant to the first and second passages 71, 72 and penetrate the base portion 2 to communicate with the outside of the main body, and the third passages 73 communicate with one of the first passages 71. Therefore, aside from allowing the ankle brace to deform correspondingly as the user walks, the ankle brace can make sure that air can flow smoothly from different directions into the first, second and third passages 71, 72, 73 to provide a great air permeability. It is understandable that a part of the first and second passages 71, 72 near an outer side of the circumferential side portion 33 are the first guiding slots 21, and a part of the first and second passages 71, 72 on an inner side of the circumferential side portion 33 are the second guiding slots 34.

More specifically, in this embodiment, the plurality of first passages 71 are equidistantly arranged, a number of the plurality of first passages 71 is three, two of the first passages 71 on relatively outer side are used to define a border of the main block 5, and one of the first passages 71 at the center overlaps with a symmetrical central line 84 of the main body 1.

Given the above, when wearing the ankle brace, the leg of the user feels more comfortable, and through the first and second guiding slots, the main body can deform slightly to match the shape of the leg. In addition, the first and second guiding slots allow air to enter and circulate so as to make sure that the ankle brace has great air permeability and can be worn for a long time.

While we have shown and described various embodiments in accordance with the present invention, it should be clear to those skilled in the art that further embodiments may be made without departing from the scope of the present invention.

What is claimed is:

1. An ankle brace, including:
a main body, having a base portion and an abutting portion for abutting against an ankle, the base portion having at least one first guiding slot, the at least one first guiding slot arranged next to the abutting portion, the abutting portion having a bottom portion, a circumferential side portion which surrounds and is connected to and between the bottom portion and the base portion and at least one second guiding slot, the bottom portion having a receiving space for receiving a part of the ankle, the circumferential side portion projecting above a slot bottom of the first guiding slot, the at least one second guiding slot being arranged on the bottom portion and penetrating the circumferential side portion and communicated with the at least one first guiding slot.

2. The ankle brace of claim 1, wherein the main body further has a first face and a second face which are opposite to each other, the first face is a plane, the abutting portion and the at least one first guiding slot are arranged on the second face, and an extension direction of the at least one first guiding slot and an extension direction of the at least one second guiding slot are parallel to the first face.

3. The ankle brace of claim 1, wherein the at least one first guiding slot penetrates the base portion to communicate with an outside of the main body.

4. The ankle brace of claim 1, wherein the main body defines a thickness direction, and on the thickness direction, the base portion is non-protrusive above the circumferential side portion.

5. The ankle brace of claim 1, wherein the main body defines a length direction, on the length direction, the base portion has a first end portion and a second end portion which are opposite to each other, a distance between the first end portion and the abutting portion is greater than a distance between the second end portion and the abutting portion, and a thickness of the base portion gradually increases from the first end portion toward the abutting portion.

6. The ankle brace of claim 1, wherein the main body is made of at least one of a soft material and a flexible material.

7. The ankle brace of claim 1, wherein along a length direction of the main body, the base portion is divided into a main block and two minor blocks, the two minor blocks are symmetrically arranged by two sides of the main block, and the abutting portion is arranged on the main block.

8. The ankle brace of claim 7, wherein a part of the main block which has the abutting portion is defined as a first block, and the rest part of the main body is defined as a second block; and an inner portion of each said minor block corresponds to the second block on a width direction of the main body, and on the width direction of the main body, a thickness of each said inner portion gradually decreases toward the second block.

9. The ankle brace of claim 7, wherein the main block has a plurality of first passages and a plurality of second passages, the first passages extend along the length direction of the main body, the second passages are perpendicular to the first passages and communicate with the first passages, each said minor block has a plurality of third passages, the third passages are slant to the first and second passages and penetrate the base portion to communicate with an outside of an main body, and the third passages communicate with one of the first passages.

10. The ankle brace of claim 9, wherein the main body further has a first face and a second face which are opposite to each other, the first face is a plane, the abutting portion and the at least one first guiding slot are arranged on the second face, and an extension direction of the at least one first guiding slot and an extension direction of the at least one second guiding slot are parallel to the first face; the at least one first guiding slot penetrates the base portion to communicate with the outside of the main body; the main body defines a thickness direction, and on the thickness direction, the base portion is non-protrusive above the circumferential side portion; the main body defines a length direction, on the length direction, the base portion has a first end portion and a second end portion which are opposite to each other, a distance between the first end portion and the abutting portion is greater than a distance between the second end portion and the abutting portion, and a thickness of the base portion gradually increases from the first end portion toward the abutting portion; a thickness of the second end portion is greater than a thickness of the first end portion and is substantially equal to a thickness of the circumferential side portion, and the thickness of the second end portion is 2 to 3 times of the thickness of the first end portion; a part of the main block which has the abutting portion is defined as a first block, and the rest part of the main body is defined as a second block, and on the width direction of the main body, a thickness of each said inner portion gradually decreases toward the second block; on the width direction of the main body, each said minor block is respectively tapered toward the first and second end portions; the plurality of first passages are equidistantly arranged, a number of the plurality of first passages is three, two of the first passages on relatively outer side are used to define a border of the main block, and one of the first passages at the center overlaps with a symmetrical central line of the main body; on the width direction of the main body, a greatest dimension of the first end portion is 2 to 3 times of a greatest dimension of the second end portion; the bottom portion is in dented dome shape, and the circumferential side portion and the bottom portion are arranged concentrically; and the main body is made of at least one of a soft material and a flexible material.

* * * * *